(12) United States Patent
Hoover

(10) Patent No.: US 6,839,982 B1
(45) Date of Patent: Jan. 11, 2005

(54) DRYER AND ATOMIZED MEDICINAL LIQUID APPARATUS FOR FEET WITH SHOE DRYING ATTACHMENT

(76) Inventor: Alford Odell Hoover, 1758 Hwy. 41 N., Winthrop, AR (US) 71866

( * ) Notice: Subject to any disclaimer, the term of this patent is extended or adjusted under 35 U.S.C. 154(b) by 0 days.

(21) Appl. No.: 10/793,243

(22) Filed: Mar. 5, 2004

Related U.S. Application Data

(63) Continuation-in-part of application No. 10/174,429, filed on Jun. 18, 2002, now Pat. No. 6,705,023.

(51) Int. Cl.[7] ................................................ F26B 19/00
(52) U.S. Cl. ........................ 34/90; 392/382; 422/295; 422/296; 422/299; 34/104; 34/91
(58) Field of Search .............................. 34/90, 91, 104; 392/379, 380, 382, 383; 422/292, 296, 299, 300, 307

(56) References Cited

U.S. PATENT DOCUMENTS

| | | | | |
|---|---|---|---|---|
| 4,136,464 A | * | 1/1979 | Hay | 34/104 |
| 4,559,440 A | * | 12/1985 | Hamasaka | 219/215 |
| 4,908,957 A | * | 3/1990 | Acosta et al. | 34/86 |
| 5,222,308 A | * | 6/1993 | Barker et al. | 34/104 |
| 5,287,636 A | * | 2/1994 | Lafleur et al. | 34/104 |
| 6,085,436 A | * | 7/2000 | Peet | 34/104 |
| 6,216,359 B1 | * | 4/2001 | Peet | 34/105 |

* cited by examiner

*Primary Examiner*—Henry Bennett
*Assistant Examiner*—Camtu Nguyen
(74) *Attorney, Agent, or Firm*—John D. Gugliotta; Olen L. York, III

(57) ABSTRACT

A combination dryer and atomized medicinal liquid apparatus and shoe or boot drying attachment, wherein the apparatus accommodates the placement of a shoe and/or boot drying attachment on an upper surface thereon. The attachment rests upon the upper surface of the dryer and atomized medicinal apparatus covering the air discharge outlets and channeling the generated air through two vertically disposed tubes. The tubes have a fixed end adjacent the attachment and a free end with an opening for transmitting or transferring the air to a shoe or boot placed thereon. A support ring circumscribes the tubes and supports a shoe(s) or boot(s) placed thereon, thereby promoting efficient drying and/or treatment of the shoe or boot by the apparatus and attachment combination.

6 Claims, 4 Drawing Sheets

DRYER AND ATOMIZED MEDICINAL LIQUID APPARATUS FOR FEET WITH SHOE DRYING ATTACHMENT

RELATED APPLICATIONS

This application is a Continuation-in-Part of prior application Ser. No. 10/174,429 filed on Jun. 18, 2002 now U.S. Pat. No. 6,705,023.

BACKGROUND OF THE INVENTION

1. Field of the Invention

The present invention relates generally to automatic drying and dispensing devices, and more particularly to a combination portable dryer and atomized medicinal liquid apparatus for feet having a shoe drying attachment.

2. Description of the Related Art

There have been many attempts at devising machines and methods for drying moisture on a person's feet and delivering foot-treating products in the prevention of fungi and other foot-related ailments. As is disclosed in the patents mentioned, there are several forms and designs of foot dryers which force heated air onto a person's foot and apply a foot-treating product at either the top or sole of the foot.

The prior art discloses foot drying devices that include substantially enclosed structures which attempt to concentrate heated air on and/or around the foot, or substantially open devices for a person to stand on. The prior art also discloses stand-alone shoe dryers, and dryers adaptable for use with standard hair dryers.

The prior art does not disclose the combination of a foot drying device capable of delivering foot-treating products, a vibrating massage, while also providing a self-sanitization feature and adaptibility for incorporating components for use in drying shoes. The present invention offers these highly desirable features.

Consequently, there exists a need for new and improved product ideas and enhancements for existing products in the foot dryer industry.

SUMMARY OF THE INVENTION

It is therefore an object of the present invention to provide an improved dryer and atomized medicinal liquid apparatus, the apparatus of light weight, thereby making the apparatus affordable to make and portable to use.

It is a further feature of the present invention to provide a dryer and atomized medicinal liquid apparatus which allows a user to simultaneously dry their feet and attend to other grooming duties, providing valuable time savings to the user.

It is a further feature of the present invention to provide a vibrating massage option to the dryer and atomized medicinal liquid apparatus.

It is a further feature of the present invention to provide a self-sanitizing option to the dryer and atomized medicinal liquid apparatus.

It is a further feature of the present invention to provide an adjustable temperature setting for the dryer and atomized medicinal liquid apparatus.

It is a further feature of the present invention to provide a pressure sensitive option for automatically starting the dryer and atomized medicinal liquid apparatus.

It is a further feature of the present invention to provide a shoe and/or boot drying attachment.

A dryer and atomized medicinal liquid apparatus includes a solid base portion, a perforated top portion, and four side walls connecting the base portion to the top portion, and forming an internal cavity for housing the interior components. The top portion includes a substantially perforated surface, which a person places their feet for drying, and a control panel for operating the device and the variable options, including temperature control and vibrational massage. The four side walls include a plurality of air intake ports by which the internal motor pulls ambient air from outside the apparatus for heating and discharge within the apparatus. The temperature control includes a setting for activating the self-sanitizing mechanism for cleaning the apparatus between uses. An internal canister holder is located along one of the side walls by which a person may insert foot-treating products. The present invention includes a pressure-sensitive means for automatic activation of the foot dryer when sufficient weight is placed onto the top portion.

Briefly described according to one embodiment of the present invention, the dryer and atomized medicinal liquid apparatus accommodates the placement of a shoe and/or boot drying attachment on an upper surface thereon. The attachment rests upon the upper surface of the dryer and atomized medicinal apparatus covering the air discharge outlets and channeling the generated air through two vertically disposed tubes. The tubes have a fixed end adjacent the attachment and a free end with an opening for transmitting or transferring the air to a shoe or boot placed thereon. A support ring circumscribes the tubes and supports a shoe(s) or boot(s) placed thereon, thereby promoting efficient drying and/or treatment of the shoe or boot by the apparatus and attachment combination.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

The best mode for carrying out the invention is presented in terms of its preferred embodiment, herein depicted within the FIGS. 1 through 4.

1. Detailed Description of the Figures

Figure 1:
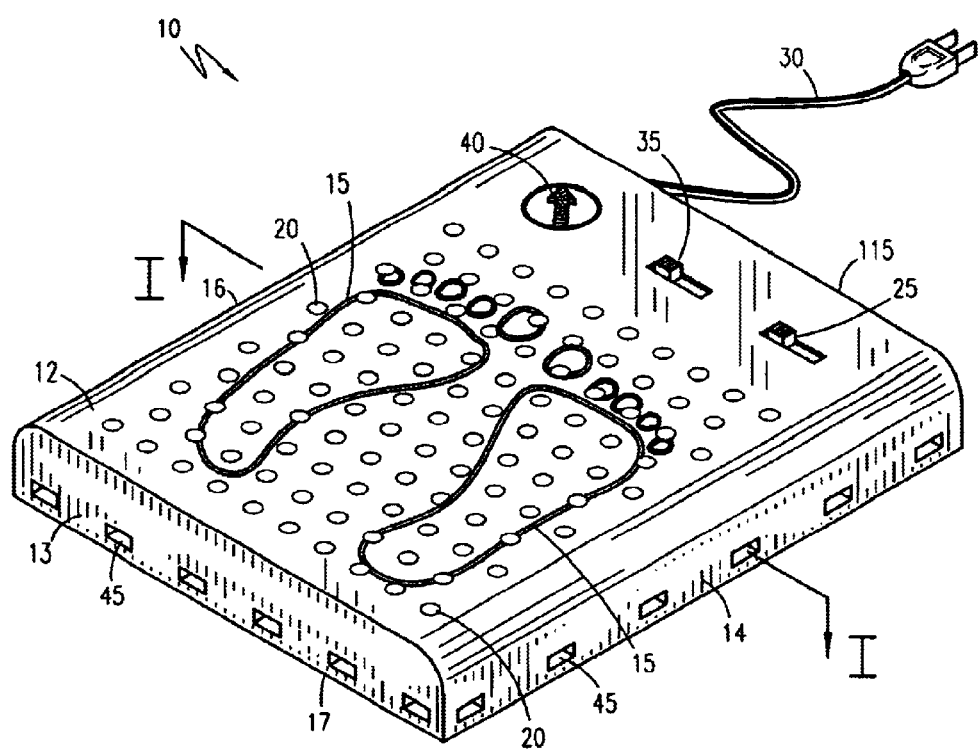
FIG. 1 is an isometric view of the dryer and atomized medicinal liquid apparatus for feet according to the preferred embodiment of the present invention.

Referring now to FIG. 1, an isometric view of the dryer and atomized medicinal liquid apparatus for feet 10 is depicted according to the preferred embodiment of the present invention. The dryer and atomized medicinal liquid apparatus for feet 10 includes a top portion 12 perpendicularly depending from four side walls 13, 14, 115, and 16, respectively, and a base portion 17 perpendicularly depending from the four side walls 13, 14, 115, and 16, respectively, and which collectively form an internal cavity 18 (not shown) for housing the internal components. The user would stand in the general position as defined by two slightly recessed footprints 15. A plurality of air discharge outlets 20 discharge a pressurized stream of warm air in conjunction with an atomized stream of antifungal or other medicinal liquid upward onto the sole area of the user's feet. At the upper or top of the dryer and atomized medicinal liquid apparatus for feet 10 along the right-hand side, an ON/OFF power switch 25 is provided to apply and remove electrical power as provided by an electrical power cord 30 to the dryer and atomized medicinal liquid apparatus for feet 10. To the left of the ON/OFF power switch 25 a vibrating massage control switch 35 is provided to apply and remove power to an internal vibrating unit as will be described in greater detail herein below. To the left of the vibrating massage control switch 35, a temperature control selector switch 40 is provided to control the temperature of the air as is discharged from the air discharge outlets 20. It is envisioned that the temperature control selector switch 40 would provide a setting of HIGH, MEDIUM and LOW, with the HIGH setting reserved to sanitize the dryer and atomized medicinal liquid apparatus for feet 10 between users. Finally, located around the base of the dryer and atomized medicinal liquid apparatus for feet 10, on all sides, is a series of air intake ports 45 which collect ambient room air for subsequent discharge through the air discharge outlets 20.

Figure 2:
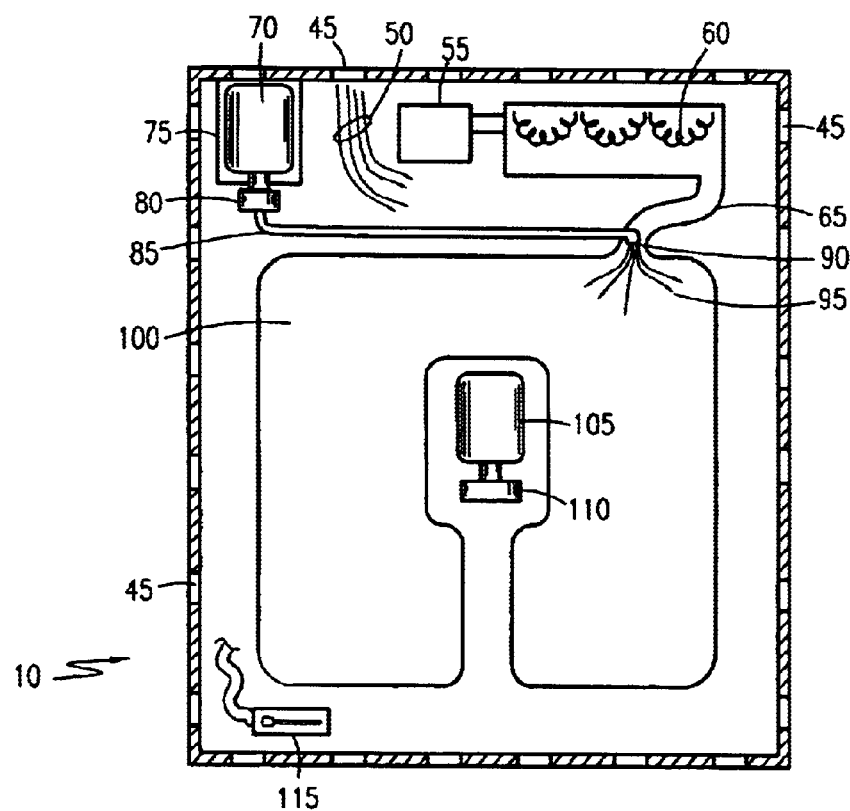
FIG. 2 is a sectional view of the dryer and atomized medicinal liquid apparatus for feet 10, as taken along a line I—I, as seen in FIG. 1.

Referring next to FIG. 2, a sectional view of the dryer and atomized medicinal liquid apparatus for feet 10, as seen along a line I—I in FIG. 1, is disclosed. Such a view depicts all interior components of the dryer and atomized medicinal liquid apparatus for feet 10 directly below the planar surface as defined by the air discharge outlets 20 (as shown in FIG. 1). Ambient room air 50 is collected through the air intake ports 45 and drawn into a motorized blower unit 55 where it is discharged, under pressure, to an enclosure containing a series of electrical resistance heaters 60. After the air passes over the electrical resistance heaters 60, it exits at a warmer temperature, envisioned to be the same temperature, or slightly lower, than a hand-held hair dryer. The warmed air exits through a transfer tube 65.

At the upper left-hand corner of the dryer and atomized medicinal liquid apparatus for feet 10, a pressurized canister of antifungal or other medicinal liquid 70 is located inside of a canister holder 75, internal to the dryer and atomized medicinal liquid apparatus for feet 10. The contents of the pressurized canister of antifungal or other medicinal liquid 70 are released under the control of an electrically operated solenoid valve 80, where it travels through a section of tubing 85 and is discharged through an atomizing nozzle 90. The atomizing nozzle 90 then produces an atomized stream of antifungal or other medicinal liquid 95 which is released at the end of the transfer tube 65 and subsequently transferred into a chamber 100. This warm stream of air, loaded with the atomized stream of antifungal or other medicinal liquid 95, then exits through the air discharge outlets 20 (as shown in FIG. 1), and onto the user's feet.

Centrally located to the dryer and atomized medicinal liquid apparatus for feet 10, and the chamber 100, are a vibrating motor 105 and an offset weight 110. When operating, the vibrating motor 105 and the offset weight 110 provide a soothing, vibrating action which is transferred to the users feet by physical contact when the users' feet are in contact with the slightly recessed footprints 15 (as shown in FIG. 1). Finally, in the lower left-hand corner of the dryer and atomized medicinal liquid apparatus for feet 10, a pressure activated micro switch 115, with associated wiring, is provided. The pressure activated micro switch 115 allows the user to simply stand upon the dryer and atomized medicinal liquid apparatus for feet 10 to activate it. In this manner, when all controls on the dryer and atomized medicinal liquid apparatus for feet 10 are preset, there is no need to bend over to activate or deactivate the dryer and atomized medicinal liquid apparatus for feet 10. This is viewed as being especially advantageous to disabled users, or users who find it difficult to bend over due to a physical ailment. When the user steps off of the dryer and atomized medicinal liquid apparatus for feet 10, it simply deactivates and is ready for use, the next time it is needed.

Figure 3:
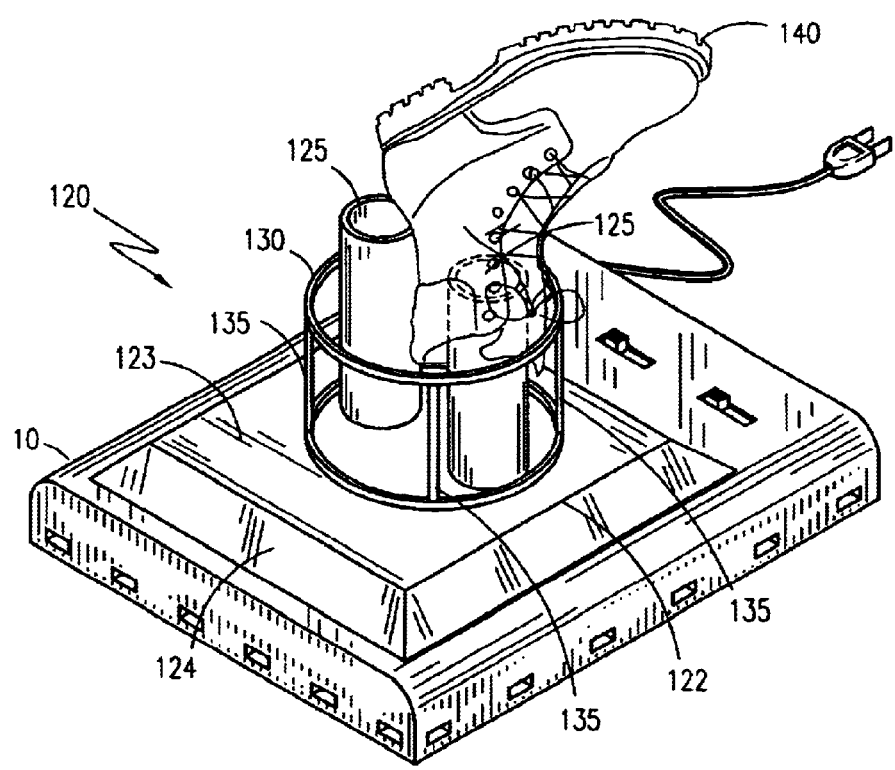
FIG. 3 is a front view of a shoe and boot drying attachment as used with the dryer and atomized medicinal liquid apparatus for feet 10.

Referring now to FIG. 3, a front view of a shoe and boot dryer attachment 120 shown in a utilized state with the dryer and atomized medicinal liquid apparatus for feet 10 is depicted. The shoe and boot dryer attachment 120 simply sits or rests atop the dryer and atomized medicinal liquid apparatus for feet 10, and is held in place by frictional contact only. The shoe and boot dryer attachment 120 includes an attachment base 122 having an upper surface 123 and downwardly depending walls 124 that channel forced air into tubes 125 (discussed below). The attachment base 122 covers all air discharge outlets 20 (as shown in FIG. 1) thus ensuring that the entire air output flow of the dryer and atomized medicinal liquid apparatus for feet 10 is routed or channeled through the shoe and boot dryer attachment 120. Two vertically disposed drying tubes 125 are provided, each of the tubes 125 having a fixed end adjacent the attachment base 122 and a free end with an opening for release of the air flow transmitted through the tubes 125. The tubes 125 transfer the entire air flow up and out through their top and opening, thus providing warmed and/or medicinally treated warm air to the shoe(s) and/or boot(s). A support ring 130, held in place by a series of supporting members 135, is provided to assist in the holding of a shoe or boot 140 in place. The support ring 130 circumscribes the tubes 125, whereby the opening in a shoe or boot fits over a tube 125 and the body of the shoe rests against the support ring 130 in the manner depicted in FIG. 3. By providing the support ring 130, thereby supporting a shoe or boot in a relatively fixed position, warmed or medicinally treated air is efficiently transmitted through the shoe or boot (as opposed to warming or treating the rear wall of the shoe. The shoe and boot dryer attachment 120 would be used with two shoes or two boots at a time, but only one is shown in FIG. 3, for purposes of diagrammatic clarity. The shoe and boot dryer attachment 120 in conjunction with the dryer and atomized medicinal liquid apparatus for feet 10, allows for the drying out of any type of shoe or boot, thus extending the life of the shoe when used under strenuous conditions, and also eliminated offensive odors as well as reducing the chance of fungus growth.

Figure 4:
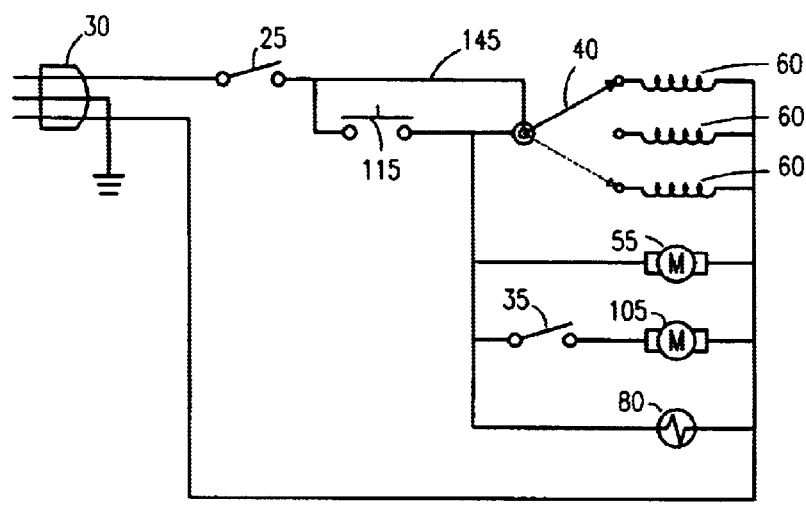
FIG. 4 is an electrical schematic diagram of the dryer and atomized medicinal liquid apparatus for feet 10.

Referring finally to FIG. 4, an electrical schematic of the dryer and atomized medicinal liquid apparatus for feet 10 is shown. Power from the electrical power cord 30 is routed through the ON/OFF power switch 25 which controls all power to the dryer and atomized medicinal liquid apparatus for feet 10 allowing it to be turned off during periods of non-use. Power is then routed through the pressure activated micro switch 115 which then applies power to four different devices. First, power is routed through the temperature control selector switch 40 where one of three different heat levels, low, medium or high is selected. Second, power is applied to the motorized blower unit 55 which provides pressurized air that flows over the electrical resistance heaters 60. Third, power is routed to the vibrating motor 105, provided the vibrating massage control switch 35 is in a closed position. This allows the user to use the dryer and atomized medicinal liquid apparatus for feet 10 without the vibrating and massage feature should it not be desired. Fourth and finally, the power is routed to the electrically operated solenoid valve 80 which releases a charge of atomized antifungal or other medicinal liquid each and every time the pressure activated micro switch 115 is activated.

A bypass circuit 145 provides power to a second deck of the temperature control selector switch 40 independent of the pressure activated micro switch 115 for use in a high heat position. This feature provides two functions. First power is routed to the high heat position to allow for sanitizing of the dryer and atomized medicinal liquid apparatus for feet 10 between users. Second, it allows use of the dryer and atomized medicinal liquid apparatus for feet 10 with the shoe and boot dryer attachment 120 (as shown in FIG. 3), without the necessity of a user standing on the dryer and atomized medicinal liquid apparatus for feet 10 to activate the pressure activated micro switch 115.

It is envisioned that other styles and configurations of the present invention can be easily incorporated into the teachings of the present invention, and only one particular configuration shall be shown and described for purposes of clarity and disclosure and not by way of limitation of scope.

2. Operation of the Preferred Embodiment

The present invention is designed with ease of operation features in mind that allow it to be utilized by a common user with little or no training or experience in a transparent manner. After acquisition of the dryer and atomized medicinal liquid apparatus for feet 10 and connecting it to a suitable electrical power source, the dryer and atomized medicinal liquid apparatus for feet 10 is ready to be set up. First, should automatic dispensing of an atomized stream of antifungal or other medicinal liquid be desired, the user must place a pressurized canister of antifungal or other medicinal liquid 70 in the canister holder 75. It is envisioned that the pressurized canister of antifungal or other medicinal liquid 70 would be available for purchase in an aerosol charged package with integral propellant. Next, the user would decide if a vibrating massage would be necessary during use of the dryer and atomized medicinal liquid apparatus for feet 10. If affirmative, the vibrating massage control switch 35 would be activated. Finally, the heat level of LOW or MEDIUM would be selected using the temperature control selector switch 40. At this point the dryer and atomized medicinal liquid apparatus for feet 10 is ready for use. It is envisioned that the dryer and atomized medicinal liquid apparatus for feet 10 would be placed in a user's bathroom near a location where activities such as drying hair, shaving or similar actions that occur after a bath or shower would take place, such as in front of a mirror. In this manner, time may be conserved by allowing a user to dry their feet, while also performing other grooming duties.

When the user steps out of the bath or shower and completes towel drying, he or she simply steps onto the dryer and atomized medicinal liquid apparatus for feet 10 which activates by the users weight as determined by the pressure activated micro switch 115. At this point warm air is directed onto the soles of the users feet by the air discharge outlets 20 which accelerates the drying process. Such drying also reduces the occurrence of moisture related ailments such as fungus, athletes' foot and the like. Should the user desire, a stream of atomized antifungal or other medicinal liquid is also directed into the airstream further reducing the occurrences of the abovementioned ailments. Finally, should the user desire, an invigorating and relaxing massage can be delivered to the users' feet. When the user steps off, the pressure activated micro switch 115 deactivates all of the abovementioned devices thus resetting the dryer and atomized medicinal liquid apparatus for feet 10 for the next time it is needed.

If the dryer and atomized medicinal liquid apparatus for feet 10 is used by many different people, the user may wish to sanitize it before use. This is accomplished by simply turning the temperature control selector switch 40 onto the HIGH position. This automatically energizes all coils of the electrical resistance heaters 60 producing a high temperature heat which would kill all bacteria on the dryer and atomized medicinal liquid apparatus for feet 10. After a suitable run time, envisioned to be approximately three minutes, the user resets the temperature control selector switch 40 to either the LOW or MEDIUM position, where it is ready for use as aforementioned described.

Should the user wish to dry shoes or boots with the dryer and atomized medicinal liquid apparatus for feet 10, the shoe and boot dryer attachment 120 is installed by simply placing it upon the dryer and atomized medicinal liquid apparatus for feet 10. Next, the shoes or boots to be dried are placed upside down on the pair of vertical drying tubes 125 as provided on the shoe and boot dryer attachment 120. The shoe or boot is held in place by the support ring 130. The user would then turn the temperature control selector switch 40 onto the HIGH heat position, where the interior of the shoes or boots would be dried. It is envisioned that a time period of approximately five minutes would be adequate to perform said drying operation. After completion of the drying cycle, the user simply removes the shoes or boots, and the shoe and boot dryer attachment 120 if needed.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents. Therefore, the scope of the invention is to be limited only by the following claims.

What is claimed is:

1. In a combination dryer and atomized medicinal liquid apparatus for feet comprising a housing formed of a top portion perpendicularly depending from four side walls and a base portion perpendicularly depending from said four side walls and which collectively form an internal cavity; two recessed footprints forming concavities in said top portion; plurality of air discharge outlets formed in said top portion for discharging a pressurized stream of warm air in conjunction with an atomized stream of antifungal or other medicinal liquid upward onto the sole area of the user's feet; a series of air intake ports formed within said sidewalls and in fluid communication with said discharge outlets, said air intake ports capable of collecting ambient room air for subsequent discharge through the air discharge outlets; a motorized blower unit housed within said housing and in fluid communication with said intakes ports for air intake and in fluid communication with said discharge outlets for air discharge; electrical resistance heaters in thermal communication with said blower unit discharge for heating discharged air; and a pressurized canister of medicinal liquid located inside of a canister holder internal to said housing such that contents of said pressurized canister are released under the control of an electrically operated solenoid valve, where it travels through a section of tubing and is discharged through an atomizing nozzle, said atomizing nozzle thereby producing an atomized stream of medicinal liquid which is released at the end of a transfer tube and subsequently transferred into a chamber;

the improvement comprising a shoe and boot dryer attachment that sits atop said dryer and atomized medicinal liquid apparatus for feet and is held in place by frictional contact only, said shoe and boot dryer attachment covering all said air discharge outlets such that the entire air output flow of said dryer and atomized medicinal liquid apparatus for feet is routed through said shoe and boot dryer attachment.

2. The improvement of claim 1, wherein said attachment comprises an attachment base having an upper surface with downwardly depending walls, said walls and said upper surface channeling forced air upward through two vertically disposed drying tubes.

3. The improvement of claim 2, wherein each one of said tubes transfers air flow upwardly to a placed shoe or boot.

4. The improvement of claim 3, wherein each one of said tubes has a fixed end adjacent an attachment base and a free end with an opening for transferring air generated by said dryer and atomized medicinal liquid apparatus.

5. The improvement of claim 3, further comprising a support ring circumscribing said tubes, said support ring provided to assist in holding a shoe or boot in place and allowing efficient transfer of air to shoe or boot.

6. The improvement of claim 1, wherein the combination of said attachment and said dryer and atomized medicinal liquid apparatus for feet allows for drying of shoes or boots, thus extending the life of the shoe or boot, eliminating offensive odors and reducing the growth of fungus.

* * * * *